(12) United States Patent
O'Doherty et al.

(10) Patent No.: US 7,693,336 B2
(45) Date of Patent: Apr. 6, 2010

(54) METHOD AND APPARATUS FOR DETERMINING IF AN OPTICAL DISK ORIGINATED FROM A VALID SOURCE

(75) Inventors: Phelim A. O'Doherty, Dublin (IE); Patrick J. Smith, Dublin (IE); Carlos Luna, Dublin (IE); Sean D. McCarthy, Dublin (IE)

(73) Assignee: Fraudhalt Limited (IE)

( * ) Notice: Subject to any disclaimer, the term of this patent is extended or adjusted under 35 U.S.C. 154(b) by 993 days.

(21) Appl. No.: 11/352,608

(22) Filed: Feb. 13, 2006

(65) Prior Publication Data

US 2006/0227993 A1 Oct. 12, 2006

Related U.S. Application Data

(63) Continuation-in-part of application No. 10/868,317, filed on Jun. 15, 2004, now Pat. No. 7,372,986.

(51) Int. Cl.
*G06K 9/36* (2006.01)
(52) U.S. Cl. ..................................... 382/232
(58) Field of Classification Search ................ 382/100, 382/141, 143, 149, 151, 218–222; 348/125–132; 369/47.22, 124.07
See application file for complete search history.

(56) References Cited

U.S. PATENT DOCUMENTS

| 4,242,662 A * | 12/1980 | Tsujiyama et al. ........... 382/149 |
| 4,481,664 A * | 11/1984 | Linger et al. ................. 382/149 |
| 4,682,794 A | 7/1987 | Margolin |
| 5,243,405 A | 9/1993 | Tichenor et al. |
| 5,907,144 A | 5/1999 | Poon et al. |
| 7,014,815 B1 * | 3/2006 | Worthington et al. ..... 422/82.05 |
| 2003/0034400 A1 | 2/2003 | Han et al. |
| 2003/0193883 A1 | 10/2003 | Parks et al. |
| 2004/0255317 A1 | 12/2004 | Benedikt et al. |

FOREIGN PATENT DOCUMENTS

WO 2004112017 A1 12/2004

* cited by examiner

*Primary Examiner*—Jose L Couso
(74) *Attorney, Agent, or Firm*—Seyfarth Shaw LLP; Brian L. Michaelis

(57) ABSTRACT

A method and apparatus for determining if an optical disk originated from a valid source, the method and apparatus scanning one major surface of the optical disk for mechanical surface imperfections, storing the locations of the surface imperfections relative to a datum, comparing a parameter of each of the locations of the surface imperfections with corresponding parameters of a master disk of known source for determining if the disk originated from the source from which the master disk originated.

20 Claims, 4 Drawing Sheets

METHOD AND APPARATUS FOR DETERMINING IF AN OPTICAL DISK ORIGINATED FROM A VALID SOURCE

RELATED APPLICATIONS

This application claims priority to and is a Continuation-in-Part of U.S. patent application Ser. No. 10/868,317 entitled "A METHOD AND APPARATUS FOR DETERMINING IF AN OPTICAL DISK ORIGINATED FROM A VALID SOURCE, filed Jun. 15, 2004, now U.S. Pat. No. 7,372,986, which is incorporated herein by reference.

FIELD OF THE INVENTION

The present invention relates to a method and apparatus for determining if an optical disk originated from a valid source.

BACKGROUND OF THE INVENTION

Due to the ready availability of duplicating equipment, counterfeiting of optical disks, in particular, counterfeiting of CD-ROMs and music CDs is becoming a major problem on a global scale. With the ever increasing sophistication of duplicating equipment, in general, it is virtually impossible to identify counterfeit software on CD-ROMs. Similar problems arise in connection with counterfeit music CDs.

SUMMARY OF THE INVENTION

The present invention is directed towards providing a method and apparatus for determining if an optical disk originated from a valid source.

According to the invention there is provided a method and apparatus for determining if an optical disk originated from a valid source, the method and apparatus scanning one major surface of the optical disk for mechanical surface imperfections, storing the locations of the surface imperfections relative to a datum, comparing a parameter of each of the locations of the surface imperfections with corresponding parameters of a master disk of known source for determining if the disk originated from the source from which the master disk originated.

In one embodiment of the invention the major surface of the disk which is scanned is the surface through which laser light is passed to the reflective surface for reading recorded data on the optical disk.

In another embodiment of the invention the major surface of the disk is scanned using dark field scanning. Preferably, scanning of the major surface is carried out by directing light towards the major surface at a relatively small angle to the major surface, so that only light incident on a surface imperfection is reflected at an angle substantially perpendicular to the major surface. Preferably, the light directed towards the surface is directed at an angle in the range of 0° to 30° to the major surface.

In one embodiment of the invention light reflected from surface imperfections on the major surface is reflected to a camera, and preferably, to a digital camera. Ideally, the disk is mounted relative to the digital camera so that one of the disk and the digital camera is moveable relative to the other in X-Y directions perpendicular to each other for facilitating scanning of the entire surface of the disk.

In one embodiment of the invention the locations of the surface imperfections are stored by their respective X-Y co-ordinates relative to the datum, and the X-Y co-ordinates are subsequently converted into angular co-ordinates of the disk.

In another embodiment of the invention the parameters of the locations are sequentially compared with corresponding stored parameters of master disks until a match has been made.

In one embodiment of the invention the datum for the disk being scanned is established relative to one of the surface imperfections, and the comparison with each master disk is made, commencing with the established datum position, and in the absence of a match, a new datum based on another surface imperfection of the disk being scanned is established and the parameters of the disk are compared with the corresponding parameters of the master disks, and preferably each surface imperfection is used as a datum.

Alternatively, the surface imperfections at each of a plurality of radii are integrated over 360° of the disk of each radius.

Additionally the invention provides apparatus for determining if an optical disk originated from a valid source, the apparatus comprising a scanning means for scanning a major surface of the disk for detecting mechanical surface imperfections, a computing means for computing the location of each surface imperfection, a secondary storing means for storing the locations of the surface imperfections, and a means for providing access to a primary storing means which stores parameters of locations of surface imperfections of master disks from known sources, and a comparing means for comparing parameters of the stored locations of the disk being scanned with corresponding parameters of the master disks for determining if the disk originated from a valid source.

In one embodiment of the invention the computing means comprises a computer.

In another embodiment of the invention the scanning means comprises a platform capable of planar movement in X-Y directions, and a camera for capturing images of surface imperfections.

In one embodiment of the invention the scanning means comprises a dark field scanner, and the dark field scanner comprises a means for directing light at the major surface of the disk at a relatively small angle to the major surface, and preferably, at an angle in the range of 0° to 30°, so that only light incident on a surface imperfection is reflected to the camera, and preferably, is reflected substantially perpendicularly from the major surface.

In one embodiment of the invention the camera is a digital camera comprising a 1,000 by 1,000 matrix of pixels, and ideally, the pixels are of 10 microns in size.

In a further embodiment of the invention the camera is capable of 2× to 10× magnification of the image, and preferably 2× to 5× magnification.

In a still further embodiment of the invention the computer carries out the comparison between the parameters of the disk and the corresponding parameters of the master disk.

In another embodiment the camera is positioned substantially to the side of the disk in order to view the stacking ring. The center of the disk is supported by a rotation stage while the edges of the disk are biased downward by a retaining ring. The biasing of the edges of the disk allow for the camera to view the vertical edge of the stacking ring, where a large portion of unique surface imperfections may exist.

In yet another embodiment of the present invention a method of processing image data obtained by the camera is presented. An image of the stacking ring is acquired by the camera. The image is then sampled and averaged, by sections of defined widths, before being recombined into a single compressed image. The compressed image becomes more manageable as well as informative as to distinguishing features of the disk itself.

Advantages of the method and apparatus according to the invention include provision of optical medium inspection for accurate determination of the source of the optical medium. A high speed inspection and magnification method and apparatus is provided for reducing substantially the incidence of optical media and software piracy.

BRIEF DESCRIPTION OF THE DRAWINGS

The foregoing and other features and advantages of the invention will be more clearly understood from the following description of an embodiment thereof, which is given by way of example only, with reference to the accompanying drawings, in which.

DETAILED DESCRIPTION

Figure 1:
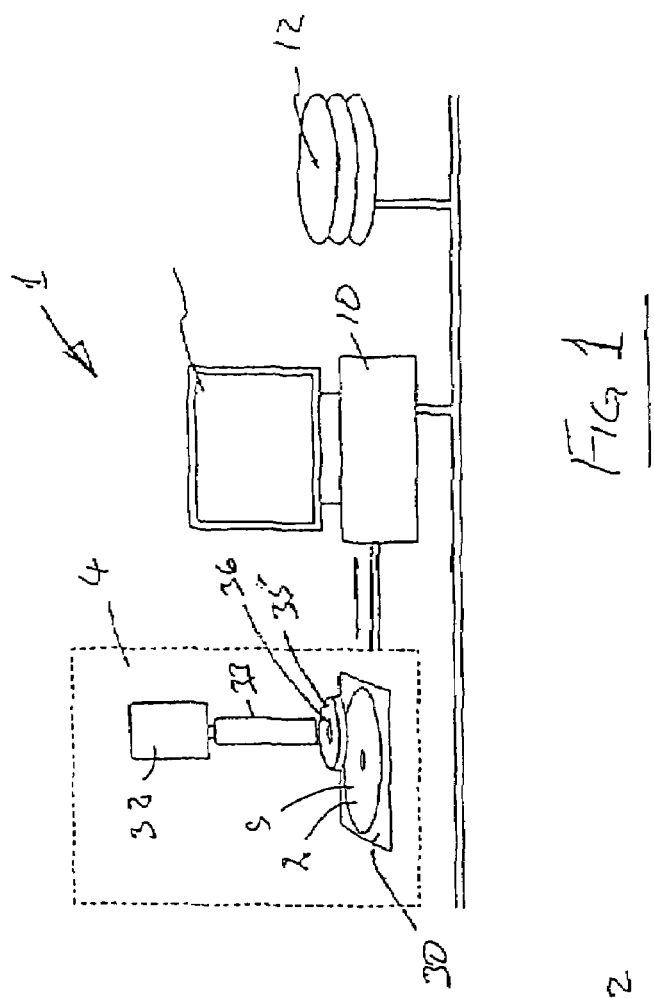
FIG. 1 is a diagrammatic representation of apparatus according to the invention for determining if an optical disk originated from a valid source.
Figure 2:
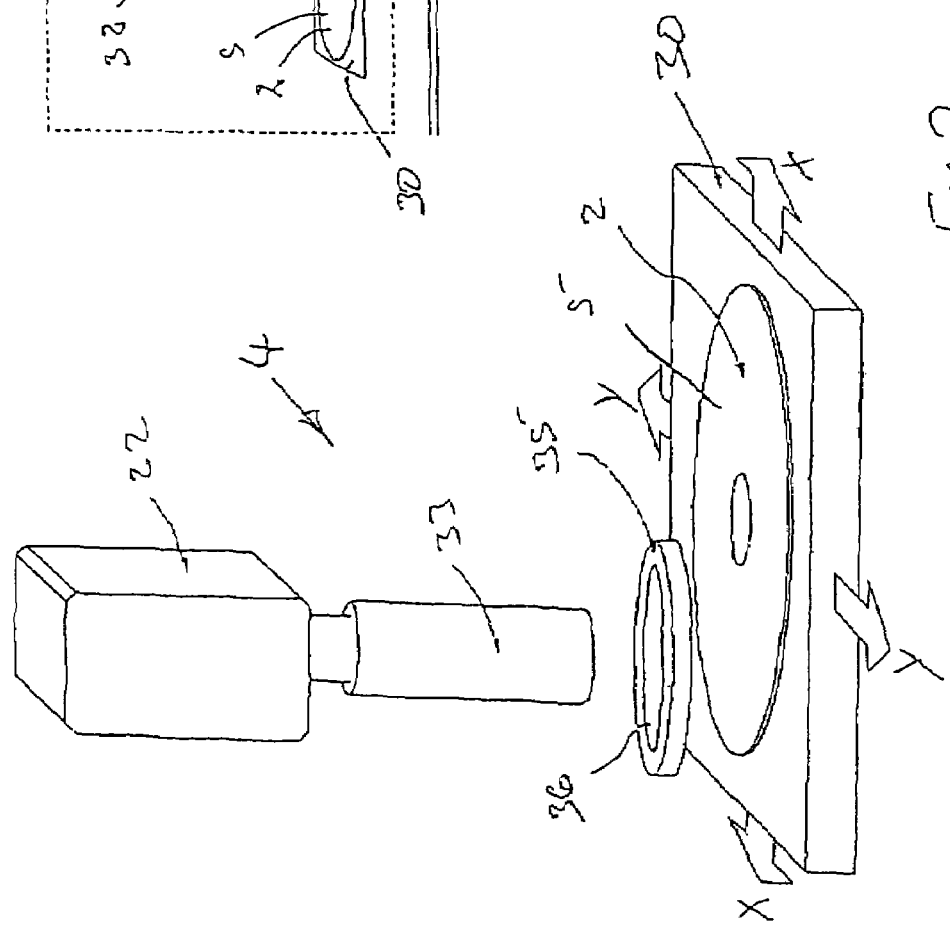
FIG. 2 is a perspective view of a portion of the apparatus of FIG. 1.

Referring to the drawings and initially to FIGS. 1 and 2, there is illustrated apparatus according to the invention, indicated generally by the reference numeral 1, for determining if an optical disk, in this embodiment of the invention a CD-ROM disk 2, originated from a valid source. The apparatus 1 comprises a dark field microscopy scanner 4 for scanning the disk 2, the validity of the origin of which is to be determined. The scanner 4, as will be described below, scans a major surface 5 of the disk 2 for identifying mechanical surface imperfections on the major surface 5, such as the imperfection 8 of the disk 2 illustrated in FIG. 4. In this embodiment of the invention the major surface 5 being scanned is the surface through which laser light is passed to the reflective surface 9 of the disk 2. A computing means, in this embodiment of the invention a PC 10 computes and stores the angular locations of the surface imperfections 8. On completion of a scan of the disk 2 the PC 10 then compares a parameter of the location of each surface imperfection with a corresponding parameter of surface imperfections of master disks stored in a primary store, namely, a read-only memory (ROM) 12 for determining if the disk 2 has originated from a valid source. The apparatus 1 and its operation will be described in more detail below, however, before proceeding to describe the apparatus 1 further, the compact disk 2 will first be described in more detail with reference to FIGS. 3 and 4.

The CD-ROM disk 2 comprises a transparent layer 15 of polycarbonate material through which laser light in use is passed to a reflective layer 16 which contains the data to be read from the CD-ROM disk 2. A label side layer 17 also of polycarbonate material is laminated to the reflective layer 16. Thus, the CD-ROM disk 2 comprises the major surface 5 on the transparent polycarbonate layer 15, and a major surface 18 on the label side 17. However, for the purpose of this embodiment of the invention only the major surface 5 on the transparent polycarbonate layer 15 is relevant. The CD-ROM disk 2 has an outer border area 20 and an inner border area 21 on which no data is recorded. A data recorded area 24 located between the inner and outer border areas 20 and 21 contains the recorded data. In this embodiment of the invention only the data recorded area 24 is scanned for mechanical surface imperfections. It has been found that mechanical presses, in which CD-ROM disks 2 are pressed, impress surface imperfections on the transparent major surface of the CD-ROM disks. These surface imperfections result from corresponding imperfections in pressing plates of the presses, and effectively form a fingerprint from which all disks pressed on a particular press can be identified. The present invention is based on this fact that each press impresses a corresponding identical pattern of surface imperfections on all disks pressed on that press.

Returning now to the apparatus 1, and referring in particular to FIGS. 1 and 2, the scanner 4 comprises a platform 30 on which the disk 2 to be scanned is secured. The platform 30 is incrementally moveable in X and Y directions for facilitating a complete scan in incremental steps of the major surface 5 of the disk 2. A camera 32, in this embodiment of the invention a digital camera, is fixedly mounted above the platform 30, and a lens 33 which provides a magnification of between 2× and 10× magnifies the image of a scanned area to the camera 32. A dark field light source provided by an annular light source 35 is located beneath the camera 32, and is co-axially aligned with the lens 33, so that light reflected perpendicularly from the major surface 5 of the disk 2 passes through a central opening 36 of the annular light source 35 to the lens 33. The annular light source 35 in this embodiment of the invention comprises a plurality of light emitting diodes which are arranged to emit light radially towards a central axis defined by the annular light source 35 at a relatively small angle to the major surface 5, which in this embodiment of the invention is approximately 30° to the major surface 5.

Figure 4:
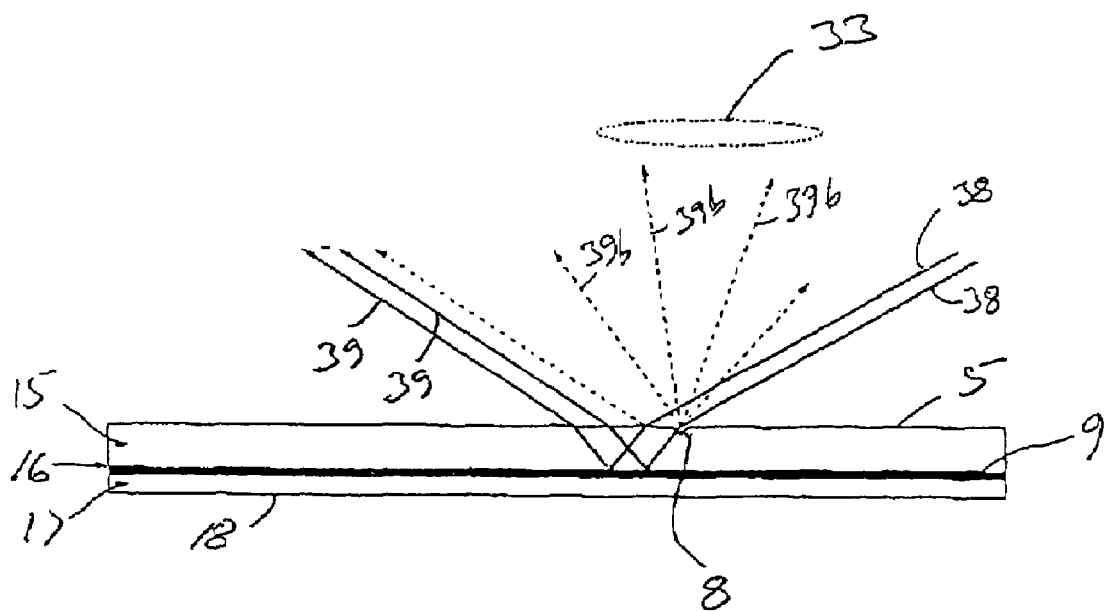
FIG. 4 is a transverse cross-sectional side elevational view of the optical disk of FIG. 3.

Light indicated by light rays 38 in FIG. 4 incident on the major surface 5 is refracted into the transparent layer 15 to the reflective layer 16 of the disk 2 and is reflected from the reflective surface 9 formed by the reflective layer 16 through the major surface 5 at an angle to the major surface 5 substantially similar to the angle of incidence of the rays 38 to the major surface 5. The reflected light is illustrated by the light rays 39. However, light from the annular light source 35 incident on a surface imperfection 8 is reflected substantially perpendicularly to the major surface 5 by the imperfection through the central opening 36 of the annular light source 35 to the lens 33, and in turn to the camera 32, (see the reflected rays 39b in FIG. 4).

Figure 3:
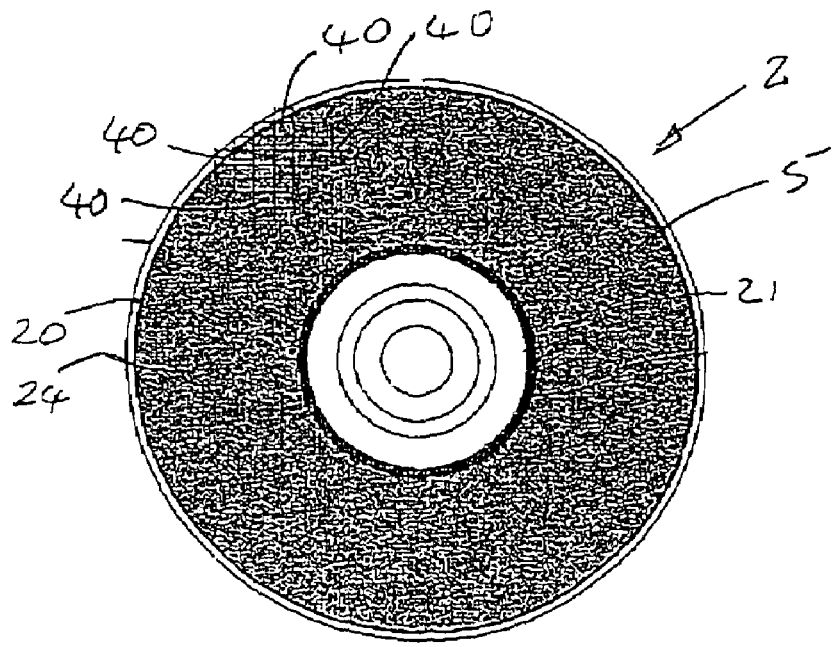
FIG. 3 is a top plan view of an optical disk.

The camera 32 is a high resolution CCD camera having a matrix of pixels of the order of $1,000^2$ of approximately 10 microns size, and when the magnification of the lens 33 is set between 2× and 5× an image 40 of approximately 2 mm to 5 mm square of the disk 2 is captured, see FIG. 3. As each image 40 is captured, the platform 30 is incremented in the appropriate X or Y direction to capture the next adjacent image 40 until the entire data recorded area 24 has been scanned. On completion of the scanning the individual image frames 40 are then pieced together by the PC to form a full map of the major surface 5 of the disk 2 which includes all the detected surface imperfections 8 and their locations on the major surface 5. The map of the major surface 5 is stored in the PC.

At this stage, any one of a number of suitable algorithms may be used for comparing the map of the major surface 5 with corresponding maps of master disks of known sources which are stored in the ROM 12 for determining if the disk 2 originated from one of the valid sources. One particularly suitable algorithm requires integrating the surface imperfections over 360° of the disk 2 at each of a number of radii from the centre of the disk 2 and comparing the integrated values at each of the radii with corresponding integrated values of the master disks to establish if a match exists. Typically, the surface imperfections are integrated over the 360° of the disk at each radius in incremental steps of 2 μm to 5 μm (object pixel size) from the inner radius of the data recorded area 24 to the outer radius of the data recorded area 24. If a match is found, then the disk 2 is deemed to have originated from a valid source. In the absence of a match being found, then the disk is deemed to be of unknown origin, and possibly counterfeit.

The PC 10 is programmable to facilitate entry and storage of additional maps of master disks, as new CD-ROM disk presses come on stream. Typically, a plurality of master disks from the same press, for example, 10 to 100 disks are scanned by the apparatus 1, and the map of the major surface of each disk is stored. Depending on the algorithm used for comparing a disk with the master disk, appropriate parameters of the locations of the imperfections are averaged over the scanned disks, and the average is then stored in an additional ROM. If, for example, the algorithm for determining if a disk originated from a valid source or otherwise is that which has already been described, the integrated values of the imperfections over the 360° of the disks at the respective radii are averaged for each radius, and the respective averages for each radius is stored.

In general, it is envisaged that it may not be possible to identify a specific datum for each disk to be tested with a datum for a master disk, and in which case, the algorithm for comparing a disk with the master disks just described is a particularly suitable algorithm. However, if it were possible to identify a specific datum for each master disk and a corresponding datum on the disk of the disk being tested, then the angular and radial locations of the respective imperfections 8 of the disk being tested can be determined from the angular datum and compared with corresponding imperfections from a corresponding angular datum on the master disk.

In use, where it is desired to determine if a disk originated from a valid source, the apparatus 1 is operated in a test mode, and the disk 2 is placed on the platform 30. The disk 2 is then scanned by the camera 32 as the platform 30 is incremented in the X and Y directions until a complete map of the data recorded area 24 of the major surface 5 of the disk 2 has been made and recorded in the PC 10. Depending on the comparison algorithm being used, the PC 10 then compares the appropriate parameters of the stored map of the disk 2 with corresponding parameters of master disks stored in the ROM 12. If a match is found, then the disk 2 is determined as having originated from a valid source. In the absence of a match, the disk is determined as being of unknown origin, and possibly counterfeit.

Where it is desired to store further master maps or master parameters of master CD-ROMs of known sources, the apparatus 1 is operated in new entry mode, and a plurality of disks, typically, 10 to 100 disks from a known source are scanned as already described and a map of the data recorded area 24 of the major surface 5 of each disk 2 is prepared and stored in the PC 10. Appropriate parameters of the surface imperfections of the scanned disks are averaged and stored in a new ROM 12.

Figure 5:
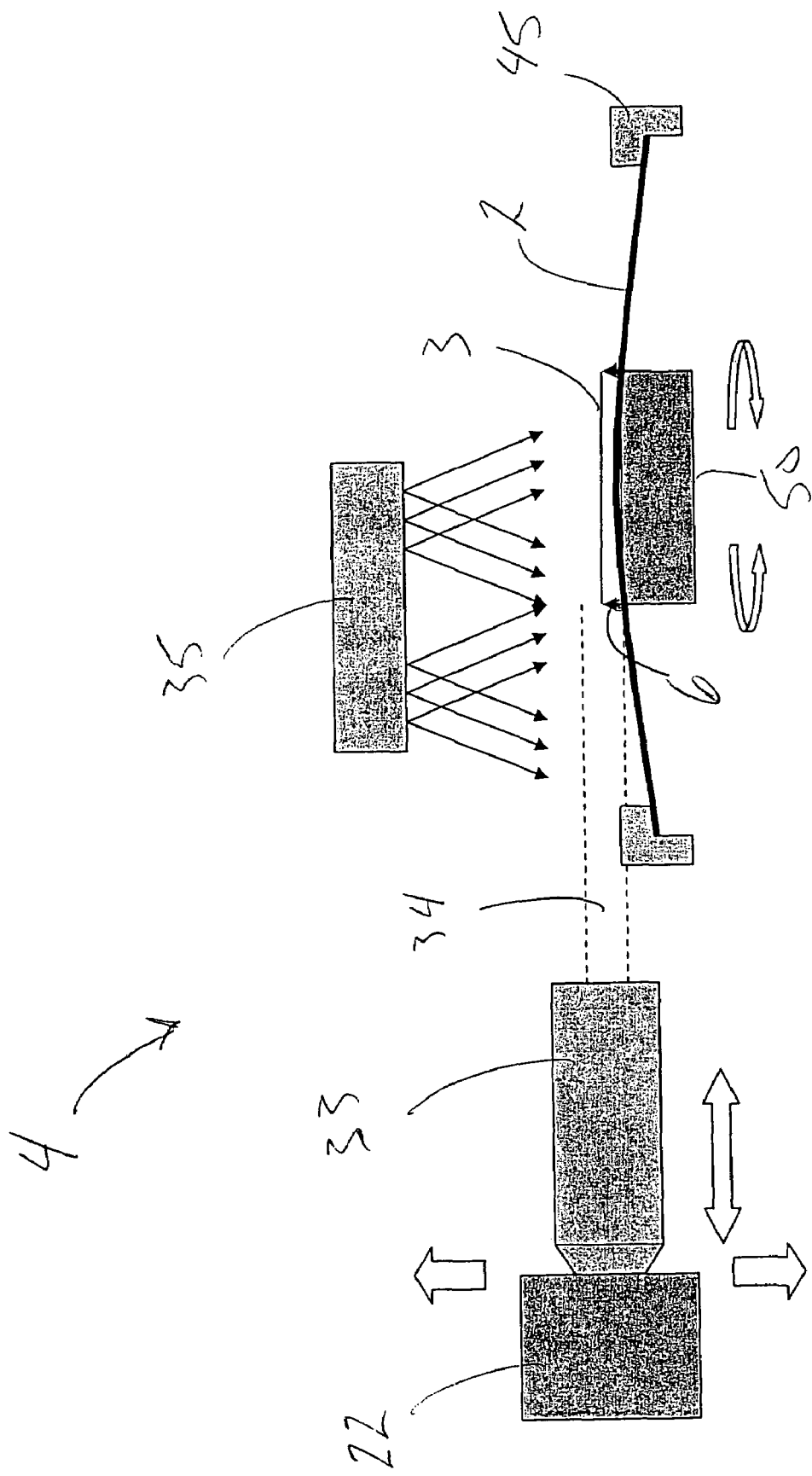
FIG. 5 is a transverse cross-sectional side view of an embodiment of the present invention.
Figure 6A:
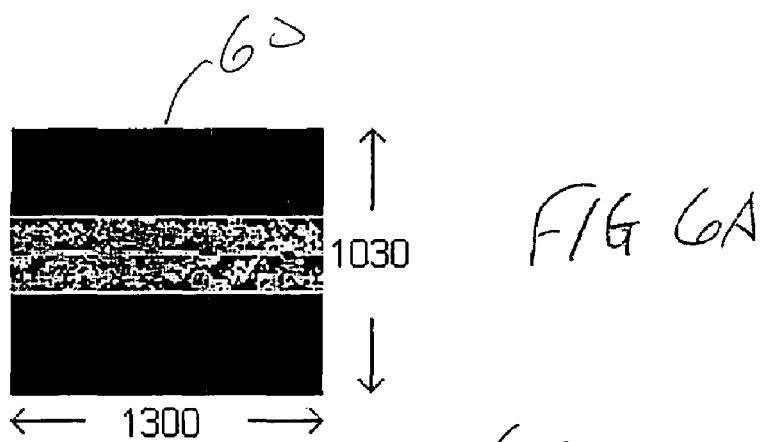
FIGS. 6A-D are a diagrammatic representation of a compression technique in accordance with an embodiment of the present invention.
Figure 6B:
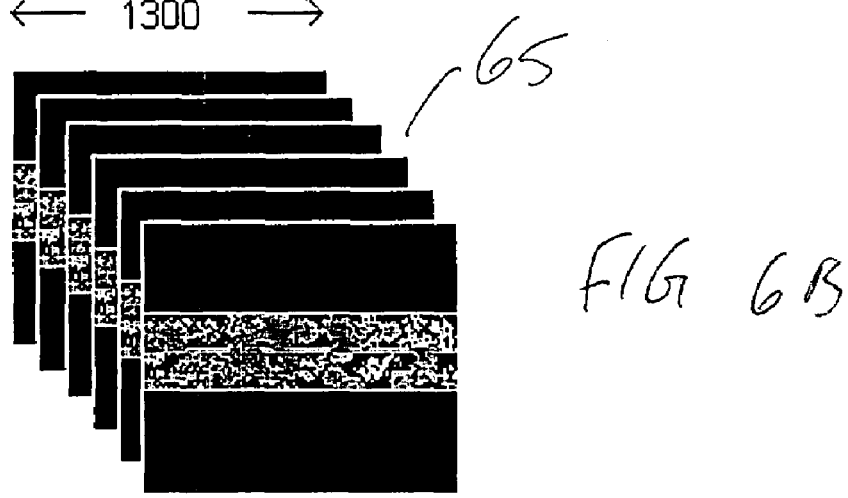
Figure 6C:
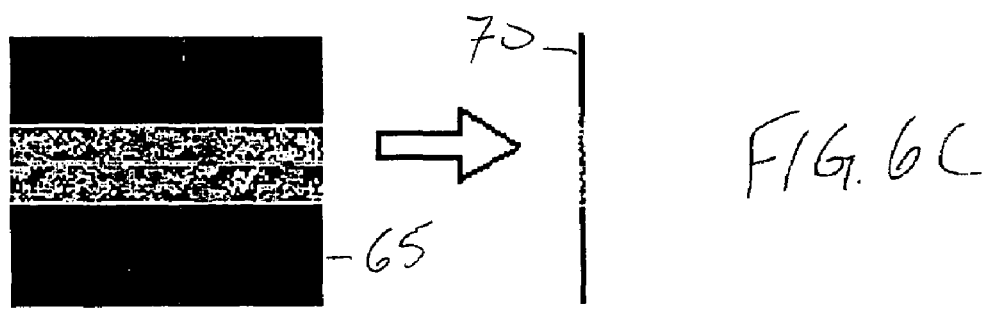
Figure 6D:
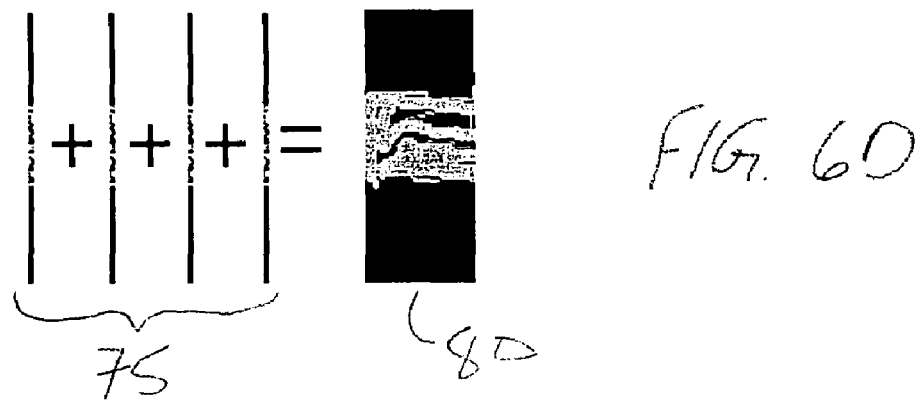

Turning now to FIG. 5, an alternative embodiment is illustrated in which the scanner 4 includes a camera 22 and lens 33 oriented to view the side of the disk 2 edge-on. This embodiment allows the camera 22 to capture distinguishing features located on the raised edges of the stacking ring 45 of the disk 2. Standard compact disk media includes a stacking ring 3 that is used to provide a small separation between each disk when they are stacked on a spindle. The stacking ring 3 rises slightly above the profile of the surface of the disk 2. The manufacturing process of compact disk media creates unique surface imperfections on the rising edge 6 of the stacking ring 3. These mechanical imperfections are less likely to be altered by the data writing or handling processes. Because this area is not subject to scratching and scuffing, the surface imperfections created during disk manufacture are used as a reference to determine the originality of the disk.

The disk 2 is mounted on a rotation stage 50 substantially near the center of the disk. In order to clear the optical path 34, the outer edge disk 2 is held down out of the way by a retaining ring 45 running around the circumference of the disk. The lens 33 is focused so as to form an image of the outer side 6 of the stacking ring 3. The stacking ring 3 is brought into focus by moving the camera 22 towards or away from the disk, and the stacking ring 3 is brought into view by adjusting the height of the camera 22 relative to the disk. The camera 22 then collects images of the raised edge 6 of the stacking ring 3 while the rotation stage 50 turns and rotates the disk 2. In one embodiment, the camera collects one image for every five degrees of rotation of the disk, yielding 72 images of the stacking ring.

Implementing this arrangement allows the system to clearly see the stacking ring 3 and distinguish it from the other parts of the disk 5. The stacking ring 3 contains vital mould features that are protected from the wear and tear during disk usage. Additionally the area of the raised edge of the stacking ring constitutes a larger continuous area than if viewed from above. The lighting of this embodiment is provided from above the disk by an annular light source 35. Strong downwards lighting from above the disk results in glancing-angle reflections from the stacking ring into the lens, effectively creating a dark-field regime. A large area ring light, for example, covers a range of incidence angles to cater for stacking rings of different slope and radius.

Scanning the disk to cover the entire stacking ring, in this embodiment requires only the rotation of the disk by the rotation stage 50 instead of moving the disk along an X-Y plane. Additionally, the camera images all sections of the raised edge 3 of the stacking ring 3 so there is no need to geometrically transform images when combining them to create a composite image. Once the images are taken by the camera, the system can analyze the images in a number of ways to reference the unique mould features of the disk material. As explained further below, the separate images can be "stitched" together to provide a large image of the entire stacking ring, or the images can be compressed into an equally distinctive and identifying image.

Turning now to FIGS. 6A-D, a sequence of images during a compression process is shown. An embodiment of the present invention compresses aggregated camera frames 65 into a single, small image 80 representing the 'fingerprint' of the stacking ring. This new smaller image shows the slow-varying features of the stacking ring and allows a quick comparison to be made between disks. The uncompressed images are saved and may be used to carry out a detailed comparison searching for additional aspects of the stacking ring.

In one embodiment, the compressed image 80 is generated by sampling and averaging the full stacking ring image in one direction. The full stacking ring image is a horizontal strip, wider than it is tall, to depict the side of the ring around its entire circumference. This strip is split into equal-sized sections 65 along its width, with each section 60 then depicting a certain angular zrange of the stacking ring. Each section is then compressed into a single column 70 of pixels by averaging along the rows of the section; that is, a pixel in the column at a given height is the average value of all the pixels in the section at that height.

The columns created are then re-combined 75 into a single compressed image 80 of the same height as the uncompressed version, but with a width equal to the number of sections it was divided into. This compressed image 80 retains and highlights features of the stacking ring which spread across a large angular range. The number of the sections used can be adjusted to create the minimal size of compressed image that retains the useful features of the stacking ring. In one embodiment, one pixel column is generated from each camera frame. For example, the frames are captured during the stepped rotation of the disk. Each frame is averaged along its pixel rows to generate a vertical strip of average-value pixels. When these are re-combined the final compressed image 80 then has a width equal to the number of camera frames used for the uncompressed image. The compressed image 80 is stored in the database along with the camera frames and/or the aggregated image.

Additional embodiments, utilize a fixed width of the uncompressed image and averages the width for each compressed column, such as 100 or 1000 pixels for example. In one embodiment, the entire uncompressed image can be averaged down to a single column to generate an 'average cross-section' through the stacking ring image. This is useful for matching stacking rings of the same design, which can be used as a pre-filtering step when matching against a library.

In addition to the increased speed in comparing a sample disk against a library, another advantage of an embodiment of the present invention is the ability to store and send disk fingerprints with low capacity memory and low bandwidth providing a more portable and pervasive imaging technology.

While the apparatus has been described as comprising a ROM which stores maps of the relevant major surface of master disks of known source, it is envisaged that in certain cases the apparatus may not include the store of data of master disks, but rather, the master disk data would be stored centrally, and the apparatus according to the invention would be able to access such a central store over a suitable communication link, for example, through a telecommunication network, the internet, or otherwise.

It is also envisaged that as disks of unknown origin are confirmed as being counterfeit, a master map or master parameters of the counterfeit disk may also be stored in the apparatus or centrally. Thus, the apparatus could also compare disks, the source of which is being determined with the master map or master parameters of the counterfeit disk in order to confirm if a disk of unknown source can be confirmed as being counterfeit.

While particular algorithms for comparing the parameters of surface imperfections of a disk with those of master disks have been described, any of various other suitable algorithms may be used.

Although the invention is described herein for determining if a CD-ROM originated from a valid source it should be appreciated that the invention could be applied to other media and packaging, such as tape and video packaging or other packaging for content that originates from a source with distinctly identifiable physical characteristics.

While the method and apparatus described herein involves use of imperfections on a major surface and/or the stacking ring of an optical disk, it should be appreciated that sub-surface imperfections or other mechanical characteristics of other surfaces or combination of surfaces may be implemented.

The invention is not limited to the embodiments hereinbefore described, which may be varied in construction and details and the foregoing and various other changes, additions or deletions in the form and function of the apparatus and method described herein and recited in the claims may be made without departing from the spirit and scope of the invention.

What is claimed:

1. A method for determining if media originated from a valid source comprising:
   collecting an image of a stacking ring by a scanner, the stacking ring having an elevation above a surface of the media;
   compressing the image by a computer averaging pixels of the image;
   storing locations of imperfections relative to a datum on at least one storage device in communication with said computer; and
   said computer comparing a parameter of each of the locations of the imperfections with corresponding parameters of a master media of known source and indicating if the media originated from the source from which the master media originated in response to said comparing.

2. The method of claim 1, wherein the pixels of the image are averaged along a row of the image, creating a compressed image with a one pixel width.

3. The method of claim 1 wherein the image of the stacking ring comprises the raised edge extending above the surface of the media.

4. The method of claim 3, wherein outer edges of the media are biased opposite the elevation of the stacking ring above the surface of the media.

5. The method according to claim 1, wherein the image of the stacking ring is scanned using dark field scanning.

6. The method according to claim 1, wherein light reflected from surface imperfections on the surface is reflected to a camera.

7. An apparatus for determining if media originated from a valid source, the apparatus comprising:
   a scanning means configured for scanning a surface of the media for detecting mechanical surface imperfections;
   a computing means in communication with said scanning means and configured for computing the location of each surface imperfection;
   a secondary storing means in communication with said computing means and configured for storing the locations of the surface imperfections; and
   a comparing means in communication with a primary storing means which stores parameters of locations of surface imperfections of master media from known sources, said comparing means configured for comparing parameters of the stored locations of the media being scanned with corresponding parameters of the master media for determining if the media originated from a valid source.

8. The apparatus according to claim 7, wherein the computing means comprises a computer.

9. The apparatus of claim 7 wherein the surface of the media for detecting mechanical imperfections is a stacking ring.

10. The apparatus of claim 9, wherein a rising edge of the stacking rings is scanned.

11. The apparatus of claim 7 wherein the scanning means is a digital camera, the digital camera disposed substantially to the side of the media, the camera obtaining a plurality of images of the surface of the media as the media is rotated an angle.

12. The apparatus of claim 11, wherein each the plurality of images is compressed, a plurality of compressed images combined to detail the mechanical imperfections of the surface of the media.

13. The apparatus according to claim 7, wherein the scanning means comprises a dark field scanner, and the dark field scanner comprises a means for directing light at the major surface of the media at a relatively small angle to the major surface.

14. The apparatus according to claim 8, wherein the scanning means comprises a dark field scanner, and the dark field scanner comprises a means for directing light at the major surface of the media at a relatively small angle to the major surface.

15. The apparatus according to claim 10, wherein the camera is capable of 2× to 10× magnification of the image.

16. A method for determining if media originated from a valid source comprising:
   collecting, by at least one computer, at least one first image of mechanical imperfections of a surface of the media from a camera, the camera disposed substantially to the side of the media such that the camera views the media substantially edge-on, the media rotated an angle for the at least one first image;
   comparing, by said at least one computer, the at least one first image with a known second image of mechanical imperfections in substantially a same orientation, the known second image of mechanical imperfections being from known media from a known valid source; and
   said at least one computer indicating if the media originated from the source from which the master media originated in response to said comparing.

17. The method of claim 16 wherein the surface of the media is a raised edge of a stacking ring.

18. The method of claim 16 wherein outer edges of the media are biased opposite the raised edge of the stacking ring.

19. The method of claim 16 further comprising:
   compressing the at least one first image by averaging pixel values along rows of the at least one first image to a one-pixel width profile;
   combining the one-pixel width profiles to create a compressed image with a pixel width equal to the plurality of images collected; and
   comparing the compressed image with a known compressed image of substantially a same orientation, the known compressed image being from known media from a known valid source.

20. The method of claim 16 wherein, the media is rotated 5 degrees for each of the plurality of images and the width of the compressed image is 72 pixels.

* * * * *